United States Patent [19]

Cohnen

[11] 4,221,798
[45] Sep. 9, 1980

[54] HYPOTENSIVE 2-HETEROCYCLOAMINO-IMIDAZOLINES

[75] Inventor: Erich Cohnen, Hamburg, Fed. Rep. of Germany

[73] Assignee: Beiersdorf Aktiengesellschaft, Hamburg, Fed. Rep. of Germany

[21] Appl. No.: 30,405

[22] Filed: Apr. 16, 1979

[30] Foreign Application Priority Data

Apr. 17, 1978 [DE] Fed. Rep. of Germany ....... 2816627
Feb. 14, 1979 [DE] Fed. Rep. of Germany ....... 2905501

[51] Int. Cl.³ .................. A61K 31/47; A61K 31/415; C07D 403/12; C07D 401/12

[52] U.S. Cl. ................. 424/258; 260/326.1; 424/273 R; 544/55; 546/143; 546/273; 548/181; 548/234; 548/316

[58] Field of Search ............ 548/316; 424/273 R, 424/258; 546/143

[56] References Cited

U.S. PATENT DOCUMENTS

| | | | |
|---|---|---|---|
| 3,509,170 | 4/1970 | Levitt | 546/143 X |
| 3,530,140 | 9/1970 | Kummer et al. | 548/316 |
| 3,674,801 | 7/1972 | Bormann et al. | 548/316 |
| 3,835,142 | 9/1974 | Wittekind et al. | 546/143 X |
| 3,846,412 | 11/1974 | Nathansohn et al. | 546/143 X |
| 3,872,121 | 3/1975 | Kummer et al. | 548/316 |
| 3,914,236 | 10/1975 | Lerch et al. | 546/143 |

FOREIGN PATENT DOCUMENTS 806060 12/1958 United Kingdom .............. 548/316

Primary Examiner—Henry R. Jiles
Assistant Examiner—Richard A. Schwartz
Attorney, Agent, or Firm—Bierman & Bierman

[57] ABSTRACT

Novel condensed nitrogen containing heterocyclic compounds and pharmaceutically acceptable acid addition salts thereof according to the following formula

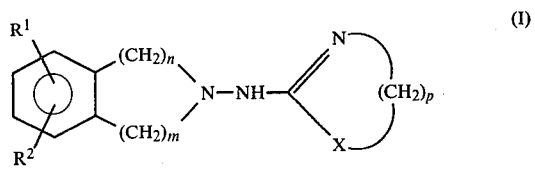

wherein $R^1$ and $R^2$ may be the same or different and are selected from hydrogen, halogen, alkyl and alkoxy having one to four carbons, X is selected from oxygen, sulfur, methylene, imino and acylimino having two to five carbons in the acyl group, n and m are positive integers of 1, 2, or 3, and p is a positive integer of 2 or 3, are disclosed which are useful as anti hypertensive agents. Compositions containing said compounds and methods of preparation are also disclosed.

10 Claims, No Drawings

HYPOTENSIVE 2-HETEROCYCLOAMINO-IMIDAZOLINES

BACKGROUND OF THE INVENTION

The invention relates to a condensed nitrogen containing heterocyclic compounds and their pharmaceutically acceptable acid addition salts which are useful as antihypertensive agents providing a long lasting hypertensive effect. Compounds containing said compounds, their method of use, and methods of preparation also form part of the present invention.

SUMMARY OF THE INVENTION

The compounds according to the present invention are represented by the following formula.

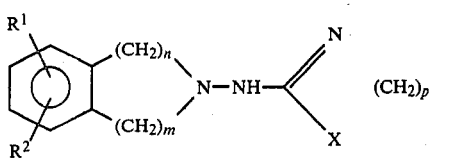

wherein $R^1$ and $R^2$ may be the same or different and are selected from hydrogen, halogen, alkyl and alkoxy having one to four carbon atoms, X is selected from oxygen, sulfur, methylene, imino and acylimino having two to five carbon atoms in the acyl group, n and m are positive integers of 1, 2 or 3, and p is a positive integer of 2 or 3.

Particularly preferred compounds of the present invention are selected from 5-chloro-2-(2-imidazolin-2-ylamino)-isoindoline, 5,6-dimethyl-2-(2-imidazolin-2-ylamino)-isoindoline, 5,6-dimethoxy-2-(imidazolin-2-ylamino)-isoindoline, 2-(2-imidazolin-2-ylamino)-1,2,3,4-tetrahydro-isoquinoline, 4-chloro-2-(2-imidazolin-2-ylamino)-isoindoline, 2-(1-acetyl-2-imidazolin-2-ylamino)-isoindoline, 3-(2-imidazolin-2-ylamino)-2,3,4,5-tetrahydro-1H-3-benzazepin, 2-(2-imidazolin-2-ylamino)2,3,4,5-tetrahydro-1H-2-benzazepin, 2-(3,4,5,6-tetrahydro-2-pyridinamino)-isoindoline, 2-(3,4-dihydro-2H-pyrrol-5-amino)-isoindoline, 2-(2-oxazolin-2-ylamino)-isoindoline, 2-(2-thiazolin-2-ylamino)-isoindoline, 2-(5,6-dihydro-4H-1,3-thiazin-2-amino)-isoindoline, and 2-(N-aminoisoindolinyl)-imidazoline.

The compounds encompassed by formula I are also useful in the form of acid addition salts. The salts can be prepared by reacting the compounds with suitable organic or inorganic acids. Preferred organic acids include fumaric acid and maleic acid. Preferred inorganic acids are the halogen hydracids such as, for example, HCl. More specifically, a hot alcohol solution of the compound is mixed with an alcohol solution of the desired acid until the reaction of the acid is well under way.

Compositions of the present compounds can be readily prepared by combining the compounds or their respective pharmaceutically acceptable acid addition salts with a pharmaceutically acceptable solid or liquid carrier. Particularly preferred carriers are selected from lactose, gelatin, corn starch, stearic acid, ethanol, propylene glycol, ethers of tetrahydrofuryl, and water.

The compounds and compositions presently contemplated may be administered to a warm blooded animal in the form of solutions for injection. Particularly preferred is peroral administration in the form of dragees, pills or tablets. Peroral administration in a dosage range of between about 1 and 10 mg/kg of body weight/day produce in rats, suffering from renal and spontaneous hypertension, a long-lasting reduction in blood pressure. A suitable dosage range for administration to humans is between about 10 and 20 mg/day and person.

The novel compounds of the present invention can be prepared according to the methods described below. In order to prepare compounds of formula I wherein $R^1$, $R^2$, n, m, and p are previously described in Formula I and X is selected from imino or acylimino, it is necessary to react a compound represented by the formula

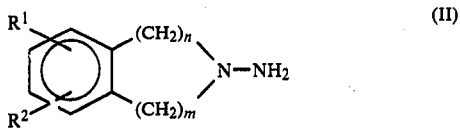

wherein $R^1$, $R^2$, n, and m are as described in Formula I with a compound of the formula

wherein $R^3$ is a nucleophilic exchangeable group, $R^4$ is selected from hydrogen and an acyl group having two to four carbon atoms, and p is a positive integer of 2 or 3. Especially preferred nucleophilic exchangeable groups are those selected from alkylthio and halogen.

Methylthio compounds are preferentially employed in this reaction, especially in the form of hydrohalide, particularly hydroiodide. Suitable acyl groups for $R^4$ are selected from acetyl, propionyl, and butyryl. Most preferred is acetyl. When it is desired to produce the present compounds where X is imino, the acyl groups may be removed by the addition of a dilute acid to the reaction system at room temperature.

The starting materials encompassed by Formula II are either known compounds or can be prepared by known methods. These compounds can also be reacted with compounds of the formula

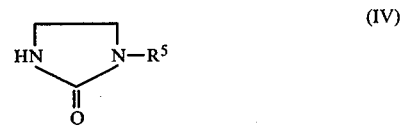

wherein $R^5$ represents an acyl group having two to four carbon atoms in order to produce the compounds of the present invention wherein p=2 and X is selected from imino and acylimino. The acyl group of $R^5$ is preferably selected from acetyl, propionyl, and butyrl with the acetyl group being the most preferred group.

The reaction is preferably carried out for between about 1 and 2 hours in the presence of a 1-acylimidazolidin-2-one and at least two moles of phosphorus oxychloride at a temperature of between about 100° C. and 120° C. If compounds having an acylimino group for X are desired, it is necessary to carefully neutralize the acid solution under ice cooling after evaporation of the phosphorus oxychloride. Compounds having an imino group for X can be obtained by removing the acyl group in the presence of a dilute acid at room temperature.

Compounds of the invention wherein X is selected from oxygen and sulfur are ultimately prepared by reacting the compounds of Formula II wherein $R^1$, $R^2$, n and m are the same as defined in Formula I with a compound of the formula $$X=C=N-(CH_2)_p-Y, \qquad (V)$$

wherein X is selected from oxygen and sulfur, Y is selected from chlorine, bromine, and iodine, and p is a positive integer of 2 or 3. Initially, compounds of the formula

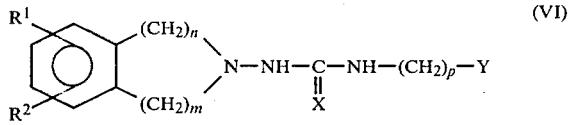

wherein $R^1$, $R^2$, n, m, and p are defined in Formula I and X and Y are defined in Formula V are produced which undergo cyclization by heating in an aqueous solution.

The compounds of Formula I wherein X is a methylene group are prepared by reacting compounds of Formula II with imino ethers of the formula

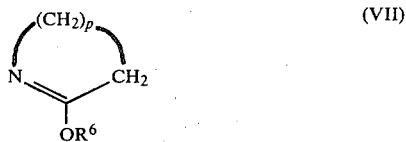

wherein $R^6$ is an alkyl group having one to four carbon atoms and p is a positive integer of 2 or 3. The reactants are heated in an inert solvent such as, for example, benzene, toluene, or xylene in a stoichiometric amount or with excess imino ether. The alcohol formed during the reaction is continually distilled and removed from the system.

The following examples are for illustrative purposes only and are not meant to limit or in anyway redefine the invention set forth in the broadest claim of the application.

EXAMPLE 1

5-chloro-2-(2-imidazolin-2-ylamino)-isoindoline 3.5 g of (0.02 M) 2-amino-5-chloro-isoindoline and 5.4 g of (0.022 M) 2-methylthio-imidazoline-hydroiodide are heated for 15 minutes to a boil in 50 ml n-amyl-alcohol. After evaporation of the solvent, the resulting residue is mixed with water, acidified with dilute hydrochloric acid, and extracted with chloroform ether. The aqueous phase is subsequently made alkaline with dilute soda lye and extracted with methylene chloride. After evaporation of the organic phase, 2.8 g of 5-chloro-2-(2-imidazolin-2-ylamino)-isoindoline as a base is obtained which is then purified by recrystallization from toluene.
Mp 178°–180° C.

In order to prepare the corresponding fumarate, 1.5 g of the resulting base are dissolved in isopropanol and mixed with fumaric acid until a reaction occurs.
Yield: 1.5 g.
Mp. 188°–189° C. (decomposition).

EXAMPLE 2

In a manner analogous to Example 1, 5,6-dimethyl-2-(2-imidazolin-2-ylamino)-isoindoline was produced.
Mp(Base): 248°–250° C.
Mp(HCl+1H$_2$O): 160°–165° C.

EXAMPLE 3

In a manner analogous to Example 1, 5,6-dimethoxy-2-(2-imidazolin-2-ylamino)-isoindoline was produced.
Mp. 191°–192° C. as maleinate.

EXAMPLE 4

2-(2-imidazolin-2-ylamino)-1,2,3,4-tetrahydro-isoquinoline 4.9 g of (0.03 M) 1,2,3,4-tetrahydro-2-amino-isoquinoline and 8.5 g of (0.035 M) 2-methylthio-imidazolin hydroiodide are heated in 40 ml of n-amyl alcohol for one hour at 120° C. After evaporation of the solvent, the resulting residue is distributed between 2 N soda lye and methylene chloride. The organic phase is separated dried and after evaporation of the solvent the residue is and boiled repeatedly with diisopropyl ether. 2-(2-imidazolin-2-ylamino-1,2,3,4-tetrahydro-isoquinoline crystallizes from the extract as a base. The base is dissolved in ethanol and reacted with fumaric acid or maleic acid to obtain the corresponding salts.
Mp. of maleinate 133°–135° C.
Mp. of fumarate 218°–222° C.

EXAMPLE 5

4-chloro-2-(2-imidazolin-2-ylamino)-isoindoline 5.2 g of (0.025 M) 2-amino-4-chloro-isoindoline-hydrochloride and 3.6 g of (0.028 M) 1-acetyl-imidazolidin-2-one are heated in 50 ml of phosphorus oxychloride for 2 hours at 100° C. After removing POCl$_3$, the resulting residue is dissolved in 100 ml of ethanol and heated to a boil for 3 hours in order to separate the acetyl group. The solvent is subsequently removed in a vacuum, the resulting residue is mixed with 2 N NaOH, and the crude base is filtered and washed with water. After extraction with hot acetic ester, 3.2 g of the pure base 4-chloro-2-(2-imidazolin-2-ylamino)-isoindoline remains as a final residue.
Mp. 160°–162° C.

In order to produce the corresponding fumarate, 2.75 g of 4-chloro-2-(2-imidazolin-2-ylamino)-isoindoline are dissolved in hot isopropanol and mixed with 1.35 g of fumaric acid in isopropanol. After cooling, the fumarate crystallizes.
Mp. 217°–218° C. (decomposition).

The hydrochloride can be produced in an analogous manner, Mp. 214° C. (decomposition).

EXAMPLE 6

2-(1-acetyl-2-imidazolin-2-ylamino)-isoindoline 3.4 g of (0.02 M) 2-amino-isoindoline-hydrochloride and 2.8 g of (0.022 M) 1-acetyl imidazoldiin-2-one are heated to a boil for 2 hours in 30 ml POCl$_3$. POCl$_3$ is withdrawn in a vacuum, and the resulting residue is mixed with ice and made basic with sodium hydrogen carbonate under ice cooling. The residue is taken up in CH$_2$Cl$_2$, washed with water, and then dried. The residue remaining after the evaporation of CH$_2$Cl$_2$ is extracted with cyclohexane. 2-(1-acetyl-2-imidazolin-2- ylamino)-isoindoline crystallizes slowly from the extract.
Mp 94°–96° C.

EXAMPLE 7

3-(2-imidazolin-2-ylamino)-2,3,4,5-tetrahydro-1H-3-benzazepin 5 g of (0.03 M) 3-amino-2,3,4,5-tetrahydro-1H-3-benzazepin and 4.3 g of (0.034 M) 1-acetyl-imidazolidin-2-one are stirred in 50 ml POCL₃ for 1 hour at 100° C. The remaining process steps are analogous to those set forth in Example 5.
Mp (base): 210°–215° C.
Mp (maleinate): 166°–167° C.

EXAMPLE 8

In a manner analogous to Example 7, 2-amino-2,3,4,5-tetrahydro-1H-2-benzazepin is used to obtain 2-(2-imidazolin-2-ylamino) 2,3,4,5-tetrahydro-1H-2-benzazepin.
Mp (base): 145°–147° C.
Mp (HCl): 183°–184° C.

EXAMPLE 9

2-(3,4,5,6-tetrahydro-2-pyridinamino)-isoindoline 1.0 g of (7.2 mM) 2-amino-isoindoline and 2.4 g of (20 mM) 2-methoxy-3,4,5,6-tetrahydro-pyridine are heated to a boil for 2 hours in 20 ml of xylene. After evaporation of the xylene, the hydrochloride is produced with enthanolic HCl. After recrystallization from acetic ester/ethanol, 1.0 g of 2-(3,4,5,6-tetrahydro-2-pyridinamino)-isoindoline is obtained.
Mp (HCl): 233°–235° C. (decomposition).

EXAMPLE 10

In a manner analogous to Example 9, 2-(3,4-dihydro-2H-pyrrol-5-amino)-isoindoline was produced.
Mp (base): 110°–112° C.
Mp (HCl): 224°–227° C.

EXAMPLE 11

2-(2-oxazolin-2-ylamino)-isoindoline 3.2 ml of (0.027 M) chlorethyl isocyanate in 15 ml of toluene are added dropwise to 5 g of (0.027 M) 2-amino-isoindoline in 100 ml toluene at a temperature of 20° to 30° C. After 1 hour, the precipitate is sucked off, washed with toluene and dried.
Yield: 7.7 g N-(2-chlorethyl)-N'-(2-isoindolinyl)-urea.
Mp: 169°–171° C. (decomposition).
Cyclization to form the corresponding oxazoline is effected by heating the urea in water until it is completely dissolved. After recrystallization from ethanol, 5 g of 2-(2-oxazolin-2-ylamino)-isoindoline is obtained.
Mp: 220°–223° C. (HCl).

EXAMPLE 12

In a manner analogous to example 11, 2-(2-thiazolin-2-ylamino)-isoindoline is produced from the corresponding chlorethyl isothiocyanate.
Mp (base): 165°–167° C.
Mp (fumarate): 210°–212° C. (decomposition).

EXAMPLE 13

In a manner analogous to example 11, 2-(5,6-dihydro-4H-1,3-thiazin-2-amino)-isoindoline is produced from the corresponding 3-chlorpropyl isothiocyanate.
Mp (HCl) 190°–192° C. (decomposition).

EXAMPLE 14

2-(N-amino-isoindolinyl)-imidazoline 15 g of (0.11 M) N-amino-isoindoline and 26.9 g of (0.11 M) 2-methylthio-imidazoline-hydroiodide are heated to boiling for 30 minutes in 200 ml n-amyl alcohol under reflux. After evaporation of the solvent, the resulting residue is distributed between methylene chloride and water. The separated organic phase is concentrated by evaporation and the resulting residue is extracted with hot benzene to remove byproducts. The sediment is then permitted to solidify. Subsequently, the hydroiodide is converted to the base by treatment with 2 N NaOH followed by filtration. After recrystallization from benzene, pure 2-(n-amino-isoindolinyl)-imidazoline is obtained.
Yield: 8.4 g.
Mp.: 160°–162° C.

In order to prepare the corresponding maleinate, 8.4 g of 2-(N-aminoisoindolinyl)-imidazoline are dissolved in hot ethanol and mixed with an ethanolic maleic acid solution until the acid reacts. After addition of ether, 2-(N-amino-isoindolinyl)-imidazoline maleinate slowly crystallizes.
Yield: 10.0 g.
Mp: 186°–187° C.

What I claim is:

1. A compound of the formula

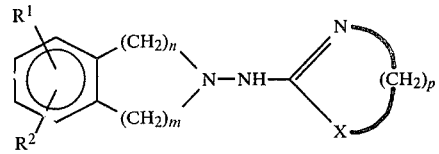

wherein R¹ and R² may be the same or different and are selected from hydrogen, halogen, alkyl and alkoxy having one to four carbons, X is imino or alkanoylimino having 2 to 5 carbon atoms in the alkanoyl group, m=1, n=1 or 2, and p is 2, or a pharmaceutically acceptable acid addition salt thereof.

2. A compound of claim 1 selected from the group consisting of 5-chloro-2-(2-imidazolin-2-ylamino)-isoindoline, 5,6-dimethyl-2-(2-imidazolin-2-ylamino)-isoindoline, 5,6-dimethyoxy-2-(imidazolin-2-ylamino)-isoindoline,2-(2-imidazolin-2-ylamino)-1,2,3,4-tetrahydro-isoquinoline, 4-chloro-2-(2-imidazolin-2-ylamino)-isoindoline, 2-(1-acetyl-2-imidazolin-2-ylamino)-isoindoline, and 2-(N-amino-isoindolinyl)-imidazoline.

3. A compound according to claim 1 wherein X is imino and n is 1.

4. A compound of claim 1 wherein said salt is selected from maleinate, fumarate, and hydrogen chloride.

5. A hypotensive composition comprising a compound of claim 1 in an amount sufficient to provide, when administered to a warm blooded animal, a therapeutically effective dose, in combination with a pharmaceutically acceptable carrier.

6. A hypotensive composition comprising a compound of claim 2 in an amount sufficient to provide, when administered to a warm blooded animal, a therapeutically effective dose, in combination with a pharmaceutically acceptable carrier.

7. The composition of claim 5 wherein said carrier is selected from lactose, gelatin, corn starch, stearic acid, ethanol, propylene glycol, ethers of tetrahydrofuryl, and water.

8. A method of lowering the blood pressure of a warm-blooded animal comprising administering to said animal a therapeutically effective amount of the compound of claim 1.

9. The method of claim 8 wherein said therapeutically effective amount is in the range of between about 1 and 20 mg/day and person.

10. The method of claim 9 wherein said amount is between about 10 and 20 mg/day and person.

* * * * *